(12) United States Patent
Schöllhorn

(10) Patent No.: US 9,651,552 B2
(45) Date of Patent: May 16, 2017

(54) ELISPOT METHOD HAVING TWO FILTER SYSTEMS

(71) Applicant: Autoimmun Diagnostika GmbH, Strassberg (DE)

(72) Inventor: Volkmar Schöllhorn, Albstadt (DE)

(73) Assignee: Autoimmun Diagnostika GmbH (DE)

( * ) Notice: Subject to any disclaimer, the term of this patent is extended or adjusted under 35 U.S.C. 154(b) by 0 days.

(21) Appl. No.: 14/810,530

(22) Filed: Jul. 28, 2015

(65) Prior Publication Data

US 2015/0338407 A1 Nov. 26, 2015

Related U.S. Application Data

(62) Division of application No. 12/740,068, filed as application No. PCT/EP2008/009112 on Oct. 29, 2008, now Pat. No. 9,207,233.

(30) Foreign Application Priority Data

Oct. 29, 2007 (DE) ........................ 10 2007 052 517

(51) Int. Cl.
| | | |
|---|---|---|
| A61K 39/04 | (2006.01) |
| A61K 39/02 | (2006.01) |
| G01N 33/53 | (2006.01) |
| G01N 33/569 | (2006.01) |
| G01N 21/64 | (2006.01) |
| G01N 33/50 | (2006.01) |

(52) U.S. Cl.
CPC ... *G01N 33/56972* (2013.01); *G01N 21/6428* (2013.01); *G01N 33/5091* (2013.01); *G01N 33/569* (2013.01); *G01N 33/50* (2013.01); *G01N 33/53* (2013.01); *G01N 2201/068* (2013.01); *G01N 2333/55* (2013.01); *G01N 2333/57* (2013.01); *G01N 2800/26* (2013.01)

(58) Field of Classification Search
CPC ......... A61K 39/00; A61K 39/02; A61K 39/04
USPC ........... 424/184.1, 234.1, 248.1; 435/7.1, 7.2
See application file for complete search history.

(56) References Cited

U.S. PATENT DOCUMENTS

| | | | |
|---|---|---|---|
| 5,784,162 A | 7/1998 | Cabib et al. |
| 5,939,281 A | 8/1999 | Lehmann et al. |
| 5,981,956 A | 11/1999 | Stern |
| 6,410,252 B1 | 6/2002 | Lehmann et al. |
| 6,642,062 B2 | 11/2003 | Kauvar et al. |
| 2003/0215791 A1 | 11/2003 | Garini et al. |
| 2004/0038241 A1 | 2/2004 | Glennsbjerg |
| 2006/0019899 A1 | 1/2006 | Storkus et al. |
| 2007/0178449 A1 | 8/2007 | Braesch-Andersen et al. |

FOREIGN PATENT DOCUMENTS

| | | |
|---|---|---|
| DE | 203 20 889 U1 | 5/2005 |
| DE | 10 2005 048 577 A1 | 4/2007 |
| EP | 0 957 359 A2 | 11/1999 |
| WO | 90/04182 A1 | 4/1990 |
| WO | 98/23960 A1 | 6/1998 |
| WO | 02/08754 A1 | 1/2002 |
| WO | 2005/045396 A2 | 5/2005 |
| WO | 2005/106482 A1 | 11/2005 |
| WO | 2007/008583 | 1/2007 |

OTHER PUBLICATIONS

Akira Shirai et al., "Individual Cells Simultaneously Produce Both IL-4 and IL-6 In Vivo," Cytokine, vol. 6, No. 1, May 1, 1994, pp. 329-336.
Pia Forsberg et al., "The outer surface proteins of Lyme disease borrelia spirochetes stimulate T cells to secrete interferon-gamma (IFNγ): diagnostic and pathogenic implications," Clin. Exp. Immunol., vol. 101, 1995, pp. 453-460.
H.L. Lipton et al., "The Predominant Virus Antigen Burden is Present in Macrophages in Theiler's Murine Encephalomyelitis Virus-Induced Demyelinating Disease," Journal of Virology, vol. 69, No. 4, Apr. 1995, pp. 2525-2533.
D.C. Douek et al., "T-cell apoptosis and differential human leucocyte antigen class II expression in human thymus," Immunology, vol. 99, 2000, pp. 249-256.
Anna Smallcombe, "BioImaging, Multicolor Imaging: The Important Question of Co-Localization," BioTechniques, vol. 30, No. 6, 2001, pp. 1240, 1242 and 1244-1246.
Irwin I. Singer et al., "CCR5, CXCR4, and CD4 Are Clustered and Closely Apposed on Microvilli of Human Macrophages and T Cells," Journal of Virology, vol. 75, No. 8, 2001, pp. 3779-3790.
Guang-lie Yang, "Fluorescence and fluorescence microscope," Optical Instruments, vol. 23, No. 2, Apr. 2001, pp. 18-29.
Andrzej Szkaradkiewicz et al., "HBcAg-specific cytokine production by CD4 T lymphocytes of children with acute and chronic hepatitis B," Virus Research, vol. 97, 2003, pp. 127-133.
Agnès Gazagne et al., "A Fluorospot assay to detect single T lymphocytes simultaneously producing multiple cytokines," Journal of Immunological Methods, vol. 283, 2003, pp. 91-98.
Z. Cui et al., "Functional configuration of fluorescence microscopy and application thereof," Medical Equipment, vol. 17, No. 9, May 28, 2004, pp. 4-6 (one sheet with English translation of Abstract).
"ELISPOT KITS—2005, Dual Color ELISPOT," cellsciences.com, Cell Sciences, Inc., Canton, MA.

(Continued)

*Primary Examiner* — Rodney P Swartz
(74) *Attorney, Agent, or Firm* — DLA Piper LLP (US)

(57) ABSTRACT

An ELISPOT method of in vitro diagnosis of tuberculosis includes enriching or separating liquid blood fraction from its cellular components including visualizing immunocompetent cells by detecting different dyes and using at least two different filter sets, each including one narrowband excitation filter and one narrowband blocking filter, wherein the narrowband excitation filter is transmissive for light provided for luminescent excitation of a respective dye and the narrowband blocking filter is transmissive for light emitted by a respective dye and measuring the number of immunocompetent cells that secrete at least interferon-γ and interleukin-2 as a reaction to an antigen by superimposing at least two two-dimensional images generated during visualization to avoid luminescence of different dyes interfering and strong luminescence being superimposed on weak luminescence.

11 Claims, 5 Drawing Sheets

(56) References Cited

OTHER PUBLICATIONS

T. Mark Doherty et al., "Effect of sample handling on analysis of cytokine responses to *Mycobacterium tuberculosis* in clinical samples using ELISA, ELISPOT and quantitative PCR," Journal of Immunological Methods, vol. 298, 2005, pp. 129-141.

F. Eun-Hyung Lee et al., ":The balance between influenza- and RSV-specific CD4 T cells secreting IL-10 or IFNγ in young and healthy-elderly subjects," Mechanisms of Ageing and Development, vol. 126, 2005, pp. 1223-1229.

Microscopy from Carl Zeiss Methods, KS ELISPOT/KS ELISPOT compact, Routine Systems for Enzyme Linked Immuno SPOT Assay Evaluations, Sep. 2005.

Microscopy U (Molecular Expressions, Optical Microscopy Primer Specialized Techniques, Fluorescence Microscopy, Apr. 4, 2005.

Chongjie Zhang et al., :Anti-Infection Immunity, Essentials for Medical Immunology, Chapter 14, May 31, 2007, pp. 296-316 (two sheets with brief English translation).

Chongjie Zhang et al., "Cytokines," Essentials for Medical Immunology, Chapter 3, May 31, 2007, pp. 58-85 (one sheet with brief English translation).

Minoru Hagegawa et al., "Systemic Sclerosis: Potential Immunologic Targets for Treating Fibrosis in Systemic Sclerosis: A Review Focused on Leukocytes and Cytokines," Seminars in Arthritis and Rheumatism, vol. 42, No, 3, 2012, pp. 281-296.

"Fluorescence Dye and Filter Database," www.micro-shop.zeiss.com, United States.

Nilssen, D. E., "B-Cell Activation in Duodenal Mucosa after Oral Cholera Vaccination in IgA Deficient Subjects with or without IgG Subclass Deficiency," *Scand. J. Immunol.*, 1993, vol. 38, pp. 201-208.

Indian Office Action dated Nov. 22, 2016, of corresponding Indian Application No. 1892/KOLNP/2010 in English.

Boulet, S., et al., "A Dual Color ELISPOT Method for the Simultaneous Detection of IL-2 and IFN-γ HIV-Specific Immune Responses," Journal of Immunological Methods, Mar. 30, 2007, 320(0), 18-29.

ELISPOT METHOD HAVING TWO FILTER SYSTEMS

RELATED APPLICATIONS

This is a divisional of U.S. Ser. No. 12/740,068, filed Jun. 15, 2010, now issued as U.S. Pat. No. 9,207,233, which is a §371 of International Application No. PCT/EP2008/009112, with an international filing date of Oct. 29, 2008 (WO 2009/056282 A1, published May 7, 2009), which is based on German Patent Application No. 10 2007 052 517.8, filed Oct. 29, 2007.

TECHNICAL FIELD

This disclosure relates to an ELISPOT method, in particular, for the in vitro diagnosis and/or in vitro therapy monitoring of infections and/or infectious diseases, and to an associated kit.

BACKGROUND

The so-called "Enzyme-linked immunospot assay" (ELISPOT) is used inter alia to measure the antigen-specific activity of blood cells. The test is usually carried out in microtiter plates having 96 wells, each well having on the bottom a membrane on which a local color reaction around individual activated cells is formed in the event of a positive outcome of the test. The evaluation is carried out by simply counting the points or by using digital image processing systems, in which case the size and intensity of the points can also be quantified in addition to the number of points. The color reaction is based on the detection of locally formed messengers, which are bound via membrane-coupled primary antibodies. These locally bound messengers are then visualized by binding a second antibody, directed against the same messenger, which is directly or indirectly coupled with a color reaction.

Until now, only the number of reactive cells has been measured in the activity measurement of cells, to be able to draw conclusions therefrom concerning their activity. In this regard, however, it has been discovered that it is not so much or not only the number of reacting cells which is important, but rather above all the quality of the reaction of the individual cells. For instance, individual cells may react very differently to the same antigen, which is manifested in the quantity of messengers released and therefore the quantity of color reactions, mentioned in the previous section, of each individual cell. EP 0 957 359 A2 describes an ELISPOT method in which not only the number of reactive cells but also the intensity of the overall reaction is determined. This allows substantially more extensive conclusions concerning the activity of the cells.

One fundamental problem of the ELISPOT method, however, relates to the targeted detection of cells that secrete two or more different messengers in the presence of an antigen. Another problem involves detecting these cells separately from other cells, which secrete only one messenger.

As already mentioned, the measurement of cells in the scope of the ELISPOT method is generally based on color reactions due to chemoluminescent or fluorescent properties of corresponding dyes. The filter systems conventionally used for chemoluminescence or fluorescence measurement are usually based on a single filter set which, in respect of the excitation and emission of a dye, is transmissive only for light of a particular wavelength range. So-called "dual filters" are by now also used. A disadvantage with this, however, is that these filters are transmissive for a comparatively wide spectral range. Since the dyes can generally absorb and emit light outside their "ideal" spectral range, using dual filters for the measurement of cells that secrete two or more different messengers leads to a significant restriction of the measurement accuracy. This problem is exacerbated by the fact that the messengers are usually secreted in different amounts by the cells.

It could therefore be helpful to provide an ELISPOT method suitable for a sensitive measurement of cells that secrete two or more different messengers.

SUMMARY

I provide an ELISPOT method of in vitro diagnosis and/or in vitro therapy monitoring of infections and/or infectious diseases including incubating eukaryotic cells with an antigen, measuring the number of immunocompetent cells which secrete at least two different cytokines as a reaction to the antigen, and in measuring the immunocompetent cells, visualizing the cells with the aid of at least two different dyes and at least two different filter sets, the filter sets including narrowband filters.

I also provide an ELISPOT kit for in vitro diagnosis and/or in vitro therapy monitoring, including at least one component for measuring immunocompetent cells which secrete at least two different cytokines in the presence of an antigen.

I further provide an ELISPOT method of in vitro diagnosis of tuberculosis comprising enriching or separating liquid blood fraction from its cellular components which comprises eukaryotic cells enriched from a blood sample, cervical smear, or bronchial lavage, incubating the eukaryotic cells with a PPD tuberculosis-specific antigen, contacting immunocompetent cells with at least two capture antibodies and at least two corresponding detection antibodies, wherein each captive antibody and its corresponding detection antibody bind to the same cytokine secreted by the immunocompetent cells as a reaction to the antigen, and wherein the at least two detection antibodies are labeled with a different dye, visualizing the immunocompetent cells by detecting the different dyes and using at least two different filter sets, the filter sets each comprising one narrowband excitation filter and one narrowband blocking filter, wherein the narrowband excitation filter is transmissive for light provided for luminescent excitation of a respective dye and the narrowband blocking filter is transmissive for light emitted by a respective dye and measuring the number of immunocompetent cells that secrete at least interferon-γ and interleukin-2 as a reaction to the antigen by superimposing at least two two-dimensional images generated during the visualization to avoid luminescence of different dyes interfering and strong luminescence superimposed on weak luminescence.

I further yet provide an ELISPOT kit for in vitro diagnosis and/or in vitro therapy monitoring of tuberculosis, comprising at least one component to measure immunocompetent cells that secrete at least interferon-γ and interleukin-2 in the presence of an antigen and at least two different dyes and different filter sets, the filter sets each comprising one narrowband excitation filter and one narrowband blocking filter, wherein the narrowband excitation filter is transmissive for light provided for luminescent excitation of the respective dye and the narrowband blocking filter is transmissive for light emitted by the respective dye, and the at least one component is selected from the group consisting of a test vessel, capture molecule, detection molecules, antigen and dye.

BRIEF DESCRIPTION OF THE DRAWINGS

Other details and features may be found in the following description of the presentation of the method with the aid of examples, in connection with the figures. The respective features may be implemented on their own, or several may be implemented in combination with one another. The figures are hereby incorporated into the content of this description by explicit reference.

The figures schematically show:

In FIGS. 1 to 8, the transmission in percent is respectively plotted on the ordinate and the wavelength in nanometers is plotted on the abscissa.

DETAILED DESCRIPTION

Figure 1:
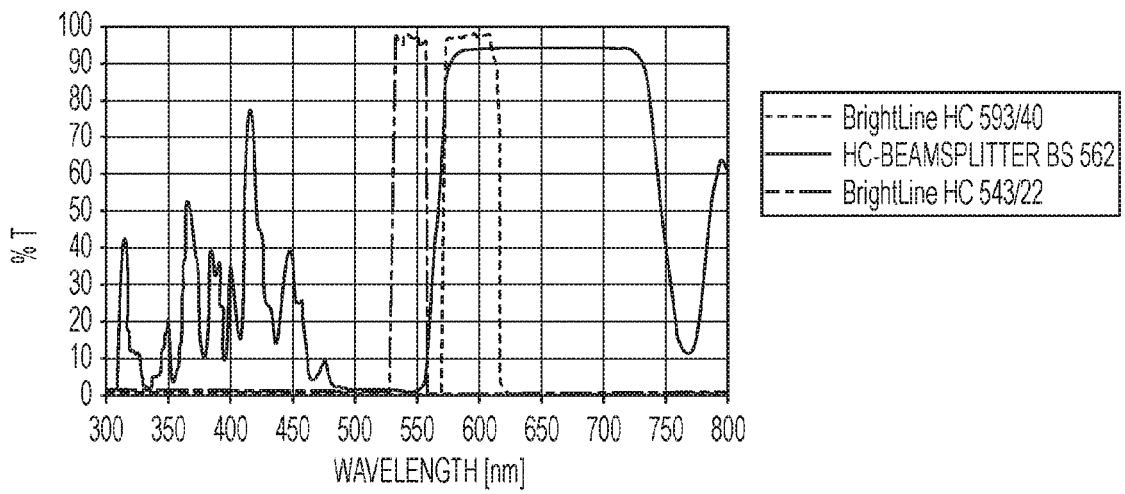
FIG. 1: The spectral properties of a set of narrowband filters (Bright Line HC 593/40, HC beam splitter BS 562, Bright Line HC 543/22, suitable for detecting the dyes cyanine 3, TRITC and Alexa 546.
Figure 2:
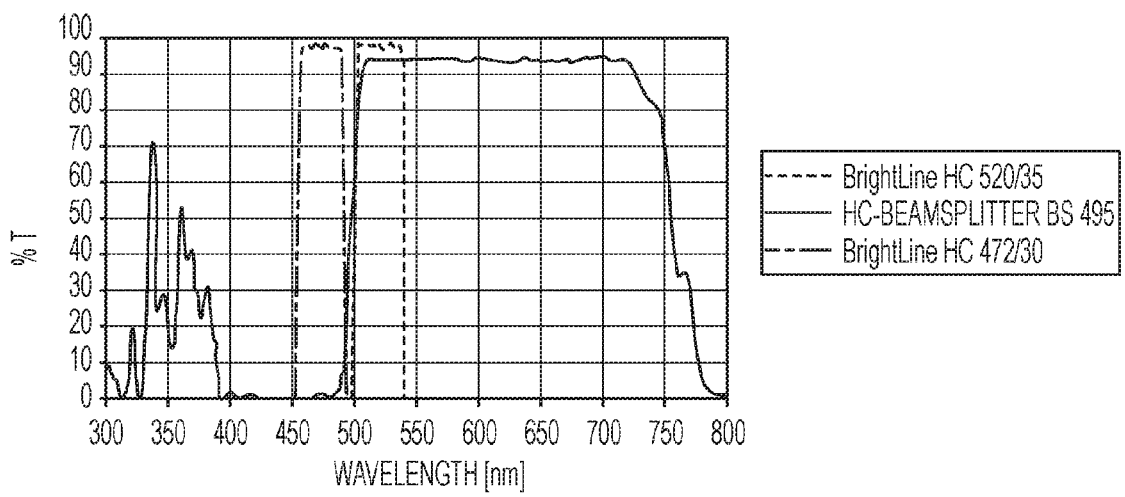
FIG. 2: The spectral properties of a set of narrowband filters (Bright Line HC 520/35, HC beam splitter BS 495 and Bright Line HC 472/30) suitable for detecting the dyes FITC, EGFP, cyanine 2 and Alexa 488.
Figure 3:
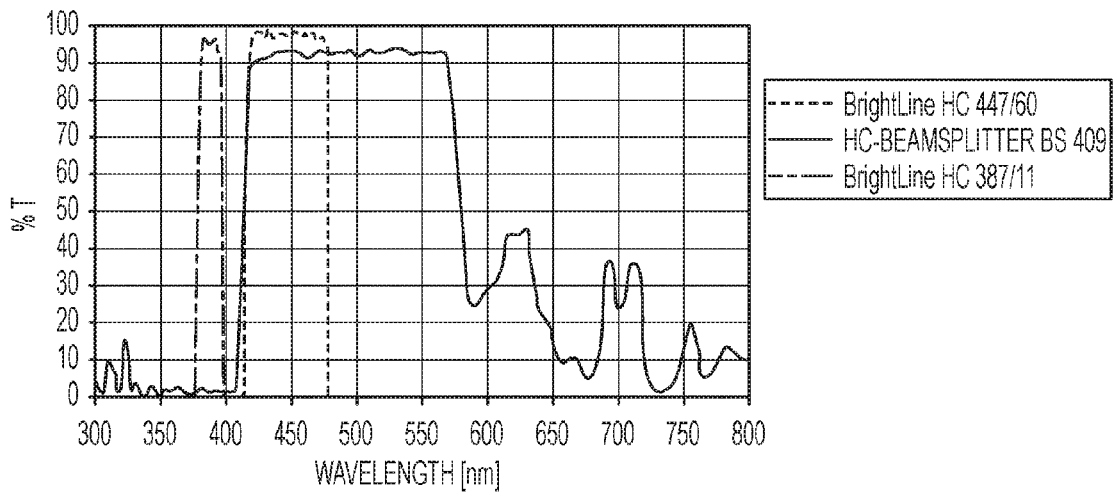
FIG. 3: The spectral properties of a set of narrowband filters (Bright Line HC 447/60, HC beamsplitter BS 409, Bright Line HC 387/11) suitable for detecting the dye DAPI.
Figure 4:
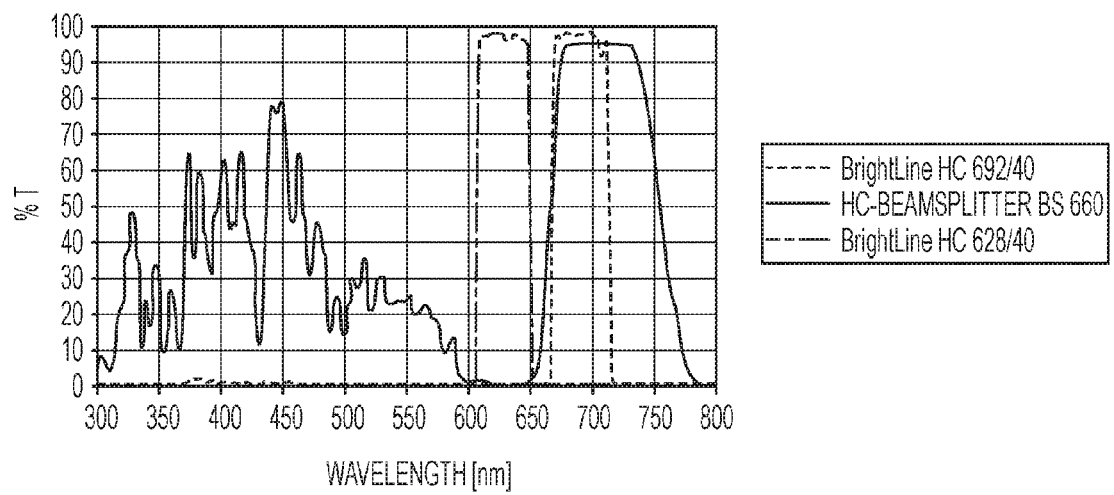
FIG. 4: The spectral properties of a set of narrowband filters (Bright Line HC 692/40, HC beam splitter BS 660, Bright Line HC 628/40) suitable for detecting the dyes cyanine 5 and Alexa 647.
Figure 5:
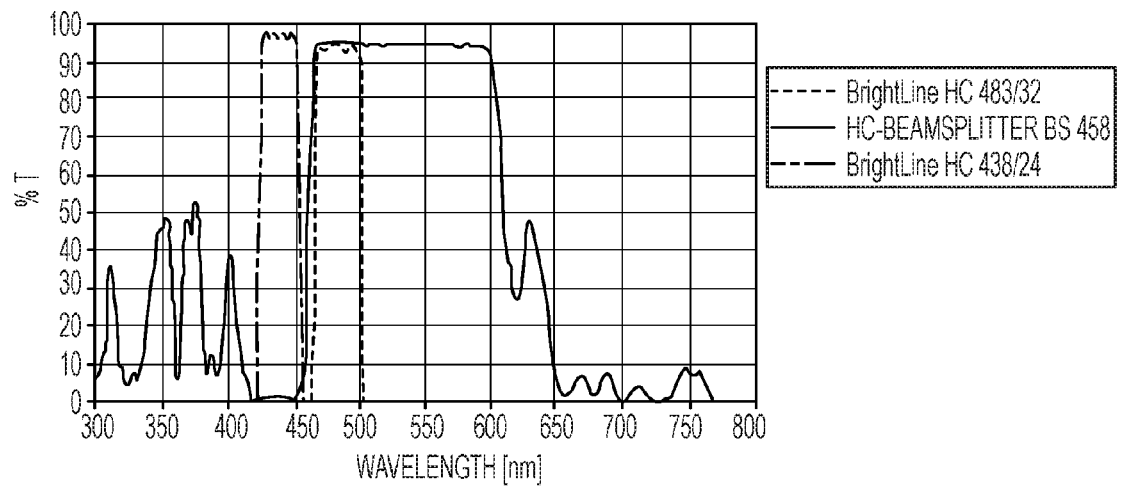
FIG. 5: The spectral properties of a set of narrowband filters (Bright Line HC 483/32, HC beam splitter BS 458, Bright Line HC 438/24) suitable for detecting the dye CFP.
Figure 6:
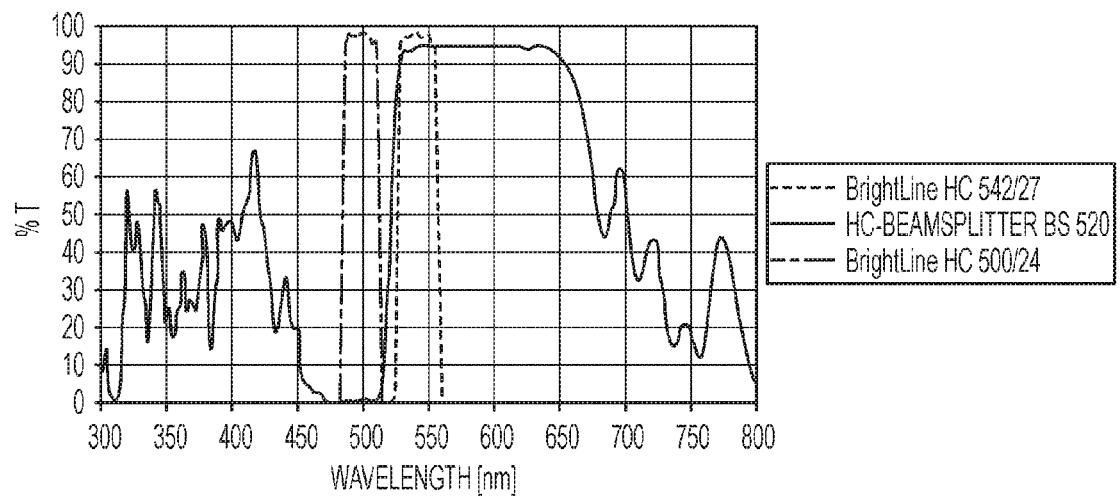
FIG. 6: The spectral properties of a set of narrowband filters (Bright Line HC 542/27, HC beam splitter BS 520, Bright Line HC 500/24) suitable for detecting the dye YFP.
Figure 7:
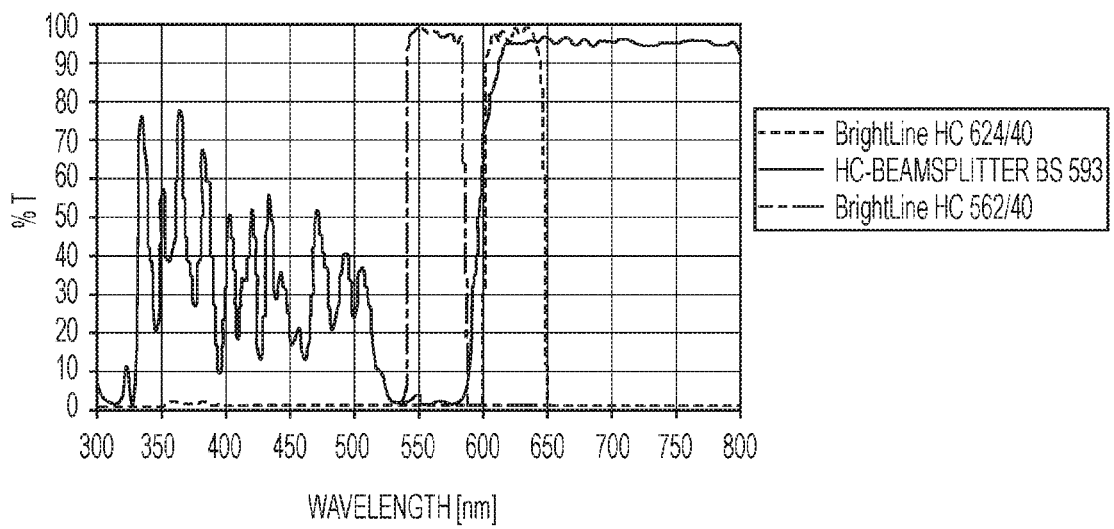
FIG. 7: The spectral properties of a set of narrowband filters (Bright Line HC 624/40, HC beam splitter BS 593, Bright Line HC 562/40) suitable for detecting the dyes Texas Red and mCherry.
Figure 8:
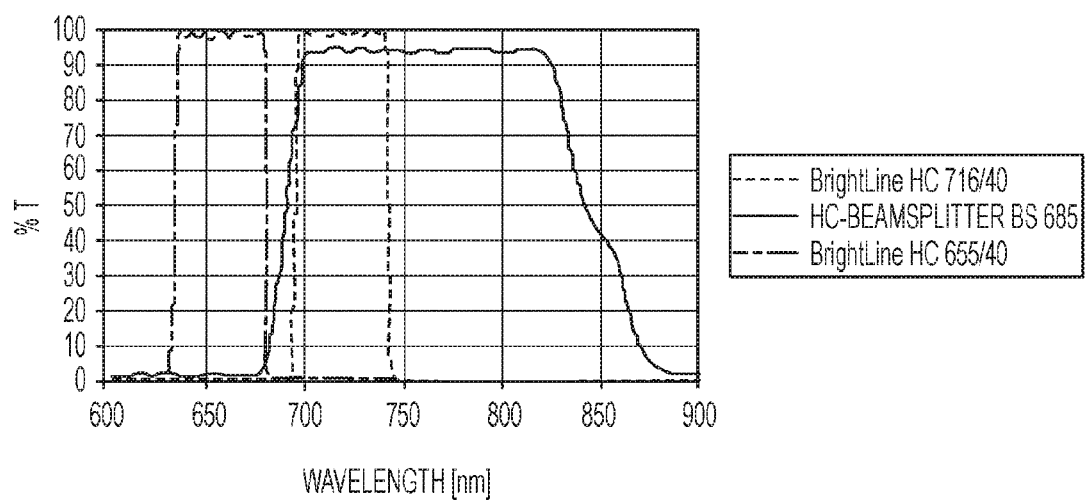
FIG. 8: The spectral properties of a set of narrowband filters (Bright Line HC 716/40, HC beam splitter BS 685, Bright Line HC 655/40) suitable for detecting the dye Cy5.5.
Figure 9:
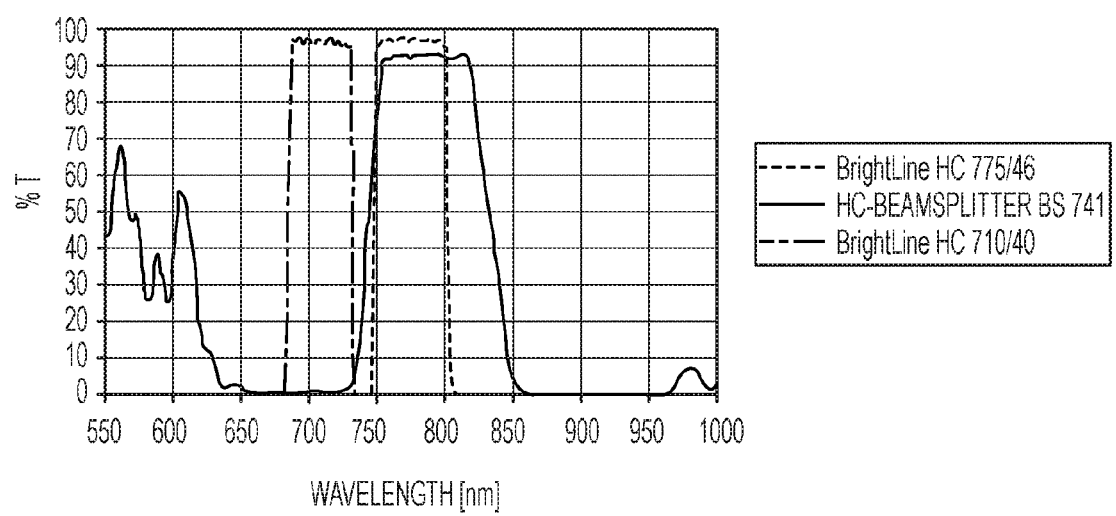
FIG. 9: The spectral properties of a set of narrowband filters (Bright Line HC 775/46, HC beam splitter BS 741, Bright Line HC 710/40) suitable for detecting the dye Cy7.

The method is an ELISPOT method ("Enzyme-linked immunospot assay"), in particular, for the in vitro diagnosis and/or in vitro therapy monitoring of infections and/or infectious diseases, characterized in that eukaryotic cells, preferably on a test surface or a carrier, are incubated with an antigen and the number of immunocompetent cells that secrete at least two different cytokines as a reaction to the antigen is measured and, in that, to measure the immunocompetent cells, they are visualized with the aid of at least two different dyes and at least two different filter sets, the filter sets comprising narrowband filters.

I provide an ELISPOT method that allows selective detection of immunocells that secrete two or more different cytokines, in relation to other immunocells that secrete only one cytokine type. The selective measurement of the immunocells is based on the use of different filter sets having narrowband filters, the limited transmission of which for excitation and emission light of dyes allows selective detection of dye luminescences, preferably dye fluorescences (narrowband filters are bandpass filters which are transmissive only for a narrow spectral range). Particularly advantageously, it is thereby possible to avoid luminescences of different dyes interfering and, in particular, strong luminescences being superimposed on weak luminescences. Compared to known ELISPOT methods, a significantly increased sensitivity is thereby achieved for immunocells that secrete two or more different cytokines in the presence of an antigen.

Particularly preferably, narrowband filters which are respectively complementary to the spectral properties of one of the dyes are used for each filter set. In this way, it is advantageously possible to avoid the aforementioned luminescence superimpositions.

In principle, the filter sets may also comprise broadband filters besides narrowband filters. For visualization of the immunocompetent cells, however, it is preferable to use filter sets that exclusively comprise narrowband filters. In another example, operation is carried out with two narrowband filters per filter set. In particular, each filter set consists of two narrowband filters.

Operation is generally carried out with different narrowband filter types in each filter set. Preferably, one narrowband excitation filter and one narrowband blocking filter are used for each filter set. The narrowband excitation filter expediently has a transmission as high as possible for light provided for luminescent excitation of the dyes. For fluorescence, longer-wavelength (low-energy) light is typically held back by this narrowband filter type and is therefore not available for excitation of the dyes. The narrowband blocking filter, on the other hand, normally has a high transmission for the light emitted by the dyes. For fluorescence, the short-wavelength (energetic) excitation light is therefore eliminated as fully as possible.

According to another example, different narrowband excitation filters are used in the filter sets, in particular, excitation filters transmissive for different light wavelength ranges. Particularly preferably, excitation filters transmissive for essentially non-over-lapping wavelength ranges of light, in particular, short-wavelength light, are used in the filter sets.

In another example, different narrowband blocking filters, in particular, narrowband blocking filters transmissive for different light wavelength ranges, are used in the filter sets. The narrowband blocking filters which may be used in the filter sets are transmissive for essentially non-overlapping wavelength ranges of light, in particular, longer-wavelength light.

All dyes having luminescent properties suitable for this may in principle be used. Chemoluminescent or fluorescent dyes are customarily used. Fluorescent dyes are preferably used. Accordingly, the chemoluminescence or fluorescence, preferably fluorescence, of dyes is normally measured.

As possible fluorescent dyes, in particular, coumarin derivatives, rhodamine derivatives, auramine derivatives, cyanines (Cy), phycoerythrin, allophycocyanin, fluorescein isothiocyanate (FITC), Texas Red, 4'-6-diamidino-2-phenylindole (DAPI), propidium iodide, Sp. green, Sp. orange, L. Yellow, green fluorescent protein (GFP), cyan fluorescent protein (CFP), yellow fluorescent protein (YFP) and/or enhanced green fluorescent protein (EGFP) may be used. Examples of suitable cyanines are cyanine 2, cyanine 3, cyanine 5.5 and/or cyanine 5. An example of a suitable rhodamine derivative is tetramethyl-rhodamine isothiocyanate (TRITC).

The following dye combinations may be used: FITC/Texas Red, DAPI/FITC, DAPI/GFP, DAPI/Cy3, DAPI/TRITC, DAPI/Texas Red, DAPI/Cy5, FITC/TRITC, Sp. green/Sp. orange, Cy2/Cy3, L. Yellow/rhodamine, FITC/Cy3, FITC/propidium iodide, FITC/Cy5 and/or Cy3/Cy5.

Fluorescence filter sets are preferably used. The usable fluorescence filters may be colored glasses (absorption filters), interference filters or combinations thereof. Interference filters are preferably employed.

According to another preferred example, to visualize the immunocompetent cells, at least one filter set having narrowband filters for fluorescein isothiocyanate and at least one filter set having narrowband filters for cyanine 3 are used. The narrowband filter provided for excitation of fluorescein isothiocyanate preferably has transmission for light in the wavelength range of 460 to 500 nm. The narrowband filter provided for the emission of fluorescein isothiocyanate preferably has transmission for light in the wavelength range of 512 to 542 nm. The preferred light transmission range for a narrowband filter provided for the excitation of cyanine 3 lies in the wavelength range of 541 to 551 nm. The light transmission range for a narrowband filter provided for the emission of cyanine 3 preferably lies in the wavelength range of 572 to 647 nm.

Customary filter sets are used which comprise a so-called "beam splitter" in addition to the narrowband filters. The beam splitter particularly advantageously ensures optimal light guiding. Thus, for fluorescence, short-wavelength light is reflected while long-wavelength light can pass almost unimpeded through the beam splitter. In this way, on the one hand, the excitation light is "deviated" in the direction of the dyes. On the other hand, the beam splitter particularly advantageously acts as an additional barrier for short-wavelength light which would otherwise interfere with visualization of immunocompetent cells. In particular, the narrowband filters which may be used, in particular, a narrowband excitation filter and a narrowband blocking filter, together with a beam splitter form a functional unit and are preferably integrated mechanically in a single element, a so-called filter block. The method may therefore in particular be carried out with at least two filter blocks of the type described above.

The filter sets may furthermore be arranged on a preferably rotatable filter wheel. Rotation of the filter wheel may, for example, be achieved using a stepper motor.

As already mentioned, an essential advantage of the method is that, according to the narrowband filter, the luminescence of a dye can be recorded specifically with its spectral properties, in particular, absorption and emission maxima, without leading to disruptive superimposition with the luminescence of another dye. Correspondingly, to visualize the immunocompetent cells, it is preferable for the luminescences of the dyes to be measured separately from one another. Preferably, to this end at least two two-dimensional images are generated per test run, in particular, per well of a microtiter plate. The two-dimensional images are usually generated by color images, generated directly in the visualization of the immunocompetent cells, being magnified and decomposed into pixels separately recorded and evaluated by a reading device. The pixels may be read out as rows. A computer can then construct a two-dimensional image from the linear values obtained. At least two two-dimensional images generated during visualization are preferably superimposed. By superimposing the images, which is usually done with the aid of suitable software, the immunocompetent cells to be measured can be identified and, in particular, distinguished from other cells.

In principle, to visualize the immunocompetent cells, the number of spots occurring on a test surface or a carrier may be determined. As an alternative to or in combination, the color intensity of individual spots or overlapping spots, and optionally colorations which cover a test surface, are preferably measured quantitatively. Particularly preferably, a test surface is decomposed into a multiplicity of individual points, the color intensity of each individual point is measured separately, and the measured intensity values are added. Up to 2 million, in particular, about 1.5 million, pixels can be recorded per test surface. The pixels may, for example, be recorded with the aid of a camera. Particularly advantageously between 200 and 300, in particular, between 220 and 260, preferably about 256 gradations (grayscale values) are available to measure the color intensity of an individual point on a test surface. Processing and evaluation of the pixels may, for example, be carried out with a reading device. Preferably, the total number of pixels and, in particular, their intensity is measured with the aid of a so-called image analyzer. In this way, it is possible to measure the overall coloration in relation to a test surface or a particular part thereof. An uncolored position on the same test surface, and optionally even on a different test surface, may be used as a reference value. As a measure of the total activity, i.e., the total intensity of the reactions of all cells on a test surface to a defined antigen, it is possible to use the product of the number of stimulated (colored) pixels and the color value (for example, grayscale levels between 0 and 256) of each stimulated pixel. This product is expediently divided by 1000 to obtain numerical values (units) which are easier to deal with. The recording and evaluation of the pixels is preferably carried out from the top, i.e., above a test surface. As already mentioned, the processing to form a two-dimensional image is usually carried out with the aid of computer technology.

Customarily, eukaryotic cells of human or animal origin are used for the incubation step. Human cells are preferably used. The eukaryotic cells generally come from a biological material to be examined. The material to be examined may consist of bodily fluids, for example, blood, lymph, synovial fluid and/or mucus secretion. The material to be examined may, for example, be a blood sample, a cervical smear or a bronchial lavage. Blood samples are preferably used. Correspondingly, it is preferable to use blood cells as eukaryotic cells. The blood cells may in particular be B-lymphocytes, T-lymphocytes, granulocytes, dendritic cells, macrophages and/or erythrocytes. Immunocompetent cells are intended, in particular, to mean immunocells, in particular, blood cells such as those mentioned in this section.

The eukaryotic cells are preferably enriched before incubation with the antigen and, in particular, freed from erythrocytes. Enrichment of the eukaryotic cells may be carried out with the aid of conventional cellular enrichment techniques. For example, the eukaryotic cells may be enriched by centrifuging, in particular, gradient centrifuging. For gradient centrifuging, for example, it is possible to use sugar gradients. In another example, the eukaryotic cells are freed from blood serum, in particular, autologous blood serum, before incubation with the antigen. On the basis of an obtained blood sample, this is usually done by separating the liquid blood fraction from the cellular constituents. In respect of the cellular constituents and suitable separation techniques, reference is made to the indications given in this paragraph.

The method is usually carried out on a suitable test surface or on a suitable carrier, particularly in a test vessel. The test surface or the carrier may, for example, consist of well bottoms of microtiter plates. Such microtiter plates, which are preferably employed as test vessels, are commercially available, in particular, with different numbers of wells. For example, the method may be carried out with the aid of a 96-well plate. Up to one million cells may be used per well of the microtiter plate. In blood, a milliliter of blood usually contains a million cells so that about 96 ml of blood may be used in the case of a 96-well plate. The microtiter plates may furthermore have a well diameter of about 5 mm corresponding to a base area of about 20 mm$^2$. The test surface is preferably flat. In this way, it is possible to avoid local concentration differences when carrying out the method. Furthermore, flat test surfaces are in principle better for generation of cellular monolayers. Typical materials, of which suitable test vessels consist are, for example, polystyrene, polyvinylidene difluoride (PVDF), nitrocellulose and nylon.

In a preferred example, at least two different capture molecules and at least two different detection molecules are used to measure the immunocompetent cells. The capture and detection molecules are preferably specific for one of the secreted cytokines. Typically, one capture molecule and one corresponding detection molecule are used for each secreted cytokine The capture and detection molecules usually bind to different sites of the secreted cytokines Ternary complex structures are generally formed in this way, consisting of capture molecules, secreted cytokines and detection molecules. Antibodies are generally used as capture and detection molecules, i.e., so-called "capture antibodies" and "detection antibodies." The capture and/or detection molecules may, in particular, be mono- and/or polyclonal antibodies. Monoclonal antibodies are preferred. The detection molecules that can be used are preferably each labeled with one of the dyes. The labeling is mostly based on covalent bonds. The detection molecules usually form a conjugate compound with the dyes, the detection molecules and the dyes preferably being bonded covalently to one another.

The number of immunocompetent cells that secrete at least two cytokine types, from the group consisting of interferons, interleukins, colony stimulating factors, tumor necrosis factors, chemokines and lymphokines, may be measured. In particular, the number of immunocompetent cells that secrete at least one interferon and at least one interleukin is measured.

Preferably, immunocompetent cells that secrete both interferon-γ and interleukin-2 are measured. These cells are preferably T cells (T lymphocytes), in particular $T_{H1}$ cells, preferably memory cells derived therefrom. This is because I surprisingly found that this cell type is present in different amounts in bodily fluids, in particular blood, during the various phases of an infection. Thus, large amounts of this cell type can be determined, above all in blood samples of persons being tested who either have been suffering from a latent infection or in whom an infection has already abated over a prolonged period of time so that the infection can essentially be regarded as having been recovered from. Typically, the blood samples of these persons comprise a proportion of between 30 and 50% or more of the cell type, expressed in terms of the total number of cells contained in the sample. On the other hand, blood samples of persons who have been suffering from an acute infection have a much lower proportion of the cell type in question.

In general, blood samples of persons tested with the aid of the method, who have been suffering from an acute infection, have a proportion of between 10 and 20% of the cell type in question, expressed in terms of the total number of cells contained in the sample. The measurement of immunocompetent cells that secrete both interferon-γ and interleukin-2 is therefore particularly advantageously suitable for an immune status assessment, particularly to distinguish between acute infections on the one hand and latent or recovered infections on the other hand. The measurement of immunocompetent cells that secrete both interferon-γ and interleukin-2 is furthermore suitable for immunization control. If many cells of the cell type can be detected, this means a good immunization status.

As possible antigens, in principle all foreign substances may be used, in particular allergens, mitogens and/or pathogen types. At least one pathogen type, in particular, at least one infectious pathogen type, is preferably used as an antigen for incubation of the eukaryotic cells. Antigens generally of microbial origin, in particular bacterial, viral and/or fungal origin, may be envisaged. As possible antigens of viral origin, it is in principle possible to use Epstein-Barr viruses, cytomegaloviruses, influenza viruses, herpes-simplex viruses, mumps viruses, rubella viruses, adenoviruses, enteroviruses, coxsackie viruses, varicella-zoster viruses and/or hepatitis viruses. Fragments of pathogen types, in particular pathogen epitopes, are preferably used as antigens. The epitopes are, in particular, peptides, preferably oligopeptides. Suitable epitopes may be made up of from 5 to 25, in particular 9 to 11, amino acid units. In a preferred example, at least one antigen from the group consisting of PPD, RD 1, RD 2, ESAT 6, CFP 10, MPT 41, MTB 64, PPE 44, OSP A, OSP B, OSP C, OSP D, OSP E, VIsE, p 58, p 100 Dbp A, HPV L1, HPV E1 to E7, influenza H1 to H15, HCV, HBV core AG NS2-6, chlamydial MOMP1 and MOMP2, is used to incubate the eukaryotic cells.

According to a particularly preferred example, at least one tuberculosis-specific antigen, in particular, from the group consisting of PPD, RD 1, RD 2, MPT 64, MTB 41 and PPE 44, is used to incubate the eukaryotic cells. In another preferred example, at least one borreliosis-specific antigen, in particular from the group consisting of VIsE, OSP A, OSP B, OSP C, OSP D and OSP E, is used to incubate the eukaryotic cells.

The infections or infectious diseases which can be diagnosed in vitro, or the therapy profile of which can be monitored in vitro, with the aid of the method are, in particular, tuberculosis, borreliosis, influenza, hepatitis A to E, herpes-simplex and/or infections and/or infectious diseases caused by cytomegaloviruses (CMV), Epstein-Barr viruses (EBV) and/or papilloma viruses, in particular, human papilloma viruses (HPV).

The method is particularly preferably suitable for immune status assessment, particularly to distinguish between acute or active infections on the one hand and latent/chronic or recovered infections on the other hand. As already mentioned, it has been possible to show that acute infections are characterized by a low number of immunocompetent cells which secrete both interferon-γ and interleukin-2, particularly in relation to cells that secrete only interferon-γ. In the case of latent infections, however, the situation is precisely the opposite.

Depending on the infection or infectious disease, different terms are customary for the infection status. In tuberculosis, for example, acute and latent infections or infectious diseases are referred to. Acute tuberculosis represents an active stage of the disease. Patients who suffer from acute tuberculosis produce tuberculosis pathogens and are infectious (contagious). Latent tuberculosis infections are not infectious in this context. It is not usually possible to detect any tuberculosis pathogens, at least not directly. In borreliosis, however, the terms active and chronic infections or infectious diseases are normally used. It is particularly preferred that the immune status can be tested by measuring the aforementioned immunocompetent cells that secrete both interferon-γ and interleukin-2 in the presence of an antigen. The method is furthermore suitable for immunization prognosis or for immunization status assessment. It is particularly advantageously possible to test whether there is sufficient immunization protection or whether re-immunization may be necessary. In respect of other features and details, reference is therefore made to the preceding description.

Lastly, this disclosure also relates to an ELISPOT kit, in particular for in vitro diagnosis and/or in vitro therapy monitoring of infections and/or infectious diseases, the kit comprising at least one component to measure immunocompetent cells that secrete at least two different cytokines in the presence of an antigen. Possible components which may be envisaged for the kit are above all suitable test vessels, capture molecules, detection molecules, antigens, dyes and filter sets having narrowband filters. In respect of other features and details concerning these components, reference is made to the preceding description.

EXAMPLE 1

Detection of Tuberculosis Pathogens

A 96-well plate is used to carry out the method. First, two different anti-antibodies are immobilized as capture molecules on the bottoms of the wells. One anti-antibody is directed specifically against interferon-γ, and the other anti-antibody is directed specifically against interleukin-2 PPD is then immobilized as a tuberculosis pathogen on the bottom of the wells. In addition or as an alternative, peptides of the so-called RD1 and RD2 complexes may also be used. Furthermore, other proteins of Mycobacterium tuberculosis (38 kD, 41 kD, 44 kD, 64 kD) may also be used. From 100,000 to 250,000 PBMCs (peripheral blood mononuclear cells) per well are subsequently added. The incubation of the blood cells (together with the tuberculosis pathogens) is carried out for a period of about 18 hours at about 37° C. The cells are then poured off and the microtiter plate washed several times. An antibody directed against interferon-γ, which is labeled covalently with fluorescein isothiocyanate, and an antibody directed against interleukin-2, which is labeled covalently with Cy3, are subsequently added. Incubation is again carried out at about 37° C. for from 4 to 12 hours. Unbound dye-labeled antibodies are subsequently washed away from the microtiter plate bottom of the 96-well plate. The fluorescences of the dyes are then measured. To this end two images are generated per well of the microtiter plate, one in the green spectral range (green fluorescence of fluorescein isothiocyanate) and one in the red spectral range (red fluorescence of Cy3). This ensures that neither weak green nor weak red fluorescences have corresponding strong red or strong green fluorescences superimposed on them. The images are subsequently superimposed. It is thereby possible to identify, and in particular quantify, immunocompetent cells that secrete both interferon-γ and interleukin-2 If the proportion of cells that secrete both interferon-γ and interleukin-2 is less than 30%, expressed in terms of the total number of cells tested overall, the cells come from patients who are suffering from acute tuberculosis. If the proportion of this cell type is above 30%, in particular above 30 to 50% or more, then the cells as a whole come either from patients who are suffering from a latent tuberculosis infection, or from patients with an already recovered infection.

EXAMPLE 2

Detection of Borrelia

A 96-well plate is used to carry out the method. Two different anti-antibodies, which respectively directed specifically against interferon-γ and interleukin-2, are immobilized on the bottoms of the wells. Borrelia-specific antigens, for example, the peptides OSP A, OSP B, OSP C, VIsE and/or internal flagellin fragment, are subsequently employed. The borrelia-specific antigens are coupled in a concentration from 1 to 10 μg/ml onto the bottoms of the wells. From 100,000 to 250,000 PBMCs (peripheral blood mononuclear cells) per well are subsequently added. The blood cells (together with the borrelia-specific antigens) are incubated for a period of about 18 hours at about 37° C. The blood cells are then poured off and the microtiter plate washed several times. An antibody directed against interferon-γ, which is labeled covalently with fluorescein isothiocyanate, and an antibody directed against interleukin-2, which is labeled covalently with Cy3, are subsequently added. Incubation is again carried out at about 37° C. for from 4 to 12 hours. Unbound dye-labeled antibodies are subsequently washed away from the microtiter plate bottom of the 96-well plate. The fluorescences of the dyes are then measured as described in Example 1. If the proportion of cells that secrete both interferon-γ and interleukin-2 is less than 30%, expressed in terms of the total number of cells tested overall, the cells come from patients who are suffering from an active borreliosis. If the proportion of this cell type is above 30%, in particular above 30 to 50% or more, then the cells as a whole come either from patients who are suffering from a chronic borreliosis infection, or from patients with an already recovered infection.

EXAMPLE 3

Detection of an Acute HPV Infection from a Cervical Smear

A 96-well plate is used to carry out the method. Two different anti-antibodies, which are respectively directed specifically against interferon-γ and interleukin-2, are immobilized on the bottoms of the wells. HPV L1 and HPV E2 to E7 are used as HPV-specific antigens. The HPV-specific antigens are coupled in a concentration from 1 to 10 μg/ml onto the bottoms of the wells. From 100 to 1000 cells per well of a washed cervical smear are then added. The cells (together with the HPV-specific antigens) are incubated for a period of about 18 hours at about 37° C. The blood cells are then poured off and the microtiter plate washed several times. An antibody directed against interferon-γ, which is labeled covalently with fluorescein isothiocyanate, and an antibody directed against interleukin-2, which is labeled covalently with Cy3, are subsequently added. Incubation is again carried out at about 37° C. for from 4 to 12 hours. Unbound dye-labeled antibodies are subsequently washed away from the microtiter plate bottom of the 96-well plate. The fluorescences of the dyes are then measured as described in Example 1. If the proportion of cells that secrete both interferon-γ and interleukin-2 is less than 30%, expressed in terms of the total number of cells tested overall, the cells come from patients who are suffering from an acute/active HPV infection. If the proportion of this cell type is above 30%, in particular above 30 to 50% or more, then the cells as a whole come either from patients who are suffering an infection which may already have persisted for months, or from patients with an already recovered infection.

The fluorescence measurements carried out in Examples 1 to 3 are respectively carried out with two filter sets, each of which is composed of a narrowband excitation filter and a narrowband blocking filter. The filters used are pure interference filters.

When the filter set contains a narrowband excitation filter with transmission of 460 to 500 nm and a narrowband blocking filter with transmission of 512 to 542 nm. These narrowband filters are adapted to the spectral properties of fluorescein isothiocyanate.

The other filter set contains a narrowband excitation filter with transmission of 541 to 551 nm and a narrowband blocking filter with transmission of 572 to 647 nm. These narrowband filters are complementary to the spectral properties of cyanine 3.

The invention claimed is:

1. An ELISPOT kit for in vitro diagnosis and/or in vitro therapy monitoring of tuberculosis, comprising at least one component to measure immunocompetent cells that secrete at least interferon-γ and interleukin-2 in the presence of a PPD tuberculosis-specific antigen and at least two different dyes and different filter sets, the filter sets each comprising one narrowband excitation filter and one narrowband blocking filter,
wherein the narrowband excitation filter is transmissive for light provided for luminescent excitation of the respective dye and the narrowband blocking filter is transmissive for light emitted by the respective dye, and the at least one component is selected from the group consisting of a test vessel, a capture molecule specific for interferon-γ, a detection molecule specific for interferon-γ, a capture molecule specific for interleukin-2, a detection molecule specific for interleukin-2, a dye and an antigen selected from the group consisting of PPD, RD 1, RD 2, MPT 64, MTB 41 and PPE 44.

2. The kit as claimed in claim 1, wherein the narrowband filters are respectively complementary to spectral properties of one of the dyes.

3. The kit as claimed in claim 1, wherein each filter set consists of one narrowband excitation filter and one narrowband blocking filter.

4. The kit as claimed in claim 1, wherein the different filter sets have different narrowband excitation filters that are transmissive for different light wavelength ranges and which do not overlap.

5. The kit as claimed in claim 1, wherein the at least two different dyes are fluorescein isothiocyanate and cyanine 3 and the kit comprises two filter sets of which one filter set has narrowband filters for fluorescein isothiocyanate and one filter set has narrowband filters for cyanine 3.

6. The kit as claimed in claim 1 comprising at least two different capture antibodies and at least two different detection antibodies.

7. The kit as claimed in claim 1, wherein the test vessel is a microtiter plate.

8. The kit as claimed in claim 1, wherein the capture molecule is a mono- or polyclonal antibody.

9. The kit as claimed in claim 1, wherein the detection molecule is a mono- or polyclonal antibody.

10. The kit as claimed in claim 1, wherein the dye is selected from the group consisting of coumarin derivatives, rhodamine derivatives, auramine derivatives, cyanines, phycoerythrin, allophycocyanin, fluorescein isothiocyanate, Texas Red, 4'-6-diamidino-2-phenylindole, propidium iodide, Sp. green, Sp. orange. L. Yellow, green fluorescent protein, cyan fluorescent protein, yellow fluorescent protein and enhanced green fluorescent protein.

11. The kit as claimed in claim 1, wherein the antigen is a peptide.

* * * * *